(12) United States Patent
Solheim et al.

(10) Patent No.: US 10,183,265 B2
(45) Date of Patent: Jan. 22, 2019

(54) METHOD AND DEVICE FOR PRETREATMENT OF BIOMASS FOR CONVERSION TO ENERGY

(71) Applicant: Cambi Technology AS, Asker (NO)

(72) Inventors: Odd Egil Solheim, Hvalstad (NO); Pål Jahre Nilsen, Bødalen (NO)

(73) Assignee: Cambi Technology AS, Asker (NO)

( * ) Notice: Subject to any disclaimer, the term of this patent is extended or adjusted under 35 U.S.C. 154(b) by 515 days.

(21) Appl. No.: 14/766,110

(22) PCT Filed: Feb. 7, 2014

(86) PCT No.: PCT/NO2014/000017
§ 371 (c)(1),
(2) Date: Aug. 5, 2015

(87) PCT Pub. No.: WO2014/123426
PCT Pub. Date: Aug. 14, 2014

(65) Prior Publication Data
US 2015/0367308 A1    Dec. 24, 2015

(30) Foreign Application Priority Data
Feb. 7, 2013   (NO) .................................. 20130207

(51) Int. Cl.
*B01J 3/00*       (2006.01)
*C02F 11/18*    (2006.01)
(Continued)

(52) U.S. Cl.
CPC ............... *B01J 3/006* (2013.01); *C02F 11/18* (2013.01); *C08H 8/00* (2013.01); *C10G 1/00* (2013.01);
(Continued)

(58) Field of Classification Search
CPC ....... B01J 3/006; C02F 11/18; C02F 2209/42; C02F 2209/03; C02F 2303/10;
(Continued)

(56) References Cited

U.S. PATENT DOCUMENTS 6,966,989 B2    11/2005   Hojsgaard et al.
2012/0111515 A1   5/2012   Nilsen et al.

FOREIGN PATENT DOCUMENTS

EP    2213631 A2    8/2010
NO    300094 B1    4/1997
(Continued)

OTHER PUBLICATIONS

Translation of the Written Opinion for PCT/NO2014/000017, dated April.*
(Continued)

*Primary Examiner* — David A Reifsnyder
(74) *Attorney, Agent, or Firm* — Winstead PC

(57) ABSTRACT

The present invention describes a method and device for pretreatment of organic material, more specific bio mass, for energy conversion, where said method comprises a first preheating step with a preheating vessel (4), a hydrolysis step with a hydrolysis reactor (5) and a pressure reducing step with a pressure reduction vessel (6), where the transfer of said organic material from the preheating vessel (4) to the hydrolysis rector (5) is effected by gravity and by creating a vacuum in the reactor (5). This method results in a very fast transfer of material from the preheating vessel (4) to the reactor (5). In addition, the filling volume of the reactor (5) is being controlled by a high frequency pressure sensor and supply of steam (3A) to the top of the reactor in order to provide the necessary head space. The invention also describes a device for performing said method.

5 Claims, 3 Drawing Sheets

(51) Int. Cl.
  *C08H 8/00* (2010.01)
  *C10G 1/00* (2006.01)
  *C10G 31/06* (2006.01)
  *C12M 1/00* (2006.01)
  *C12M 1/33* (2006.01)
  *D21C 1/02* (2006.01)

(52) U.S. Cl.
  CPC ............. *C10G 31/06* (2013.01); *C12M 45/02* (2013.01); *C12M 45/06* (2013.01); *C12M 45/20* (2013.01); *D21C 1/02* (2013.01); *C02F 2209/03* (2013.01); *C02F 2209/42* (2013.01); *C02F 2303/10* (2013.01); *Y02W 10/30* (2015.05)

(58) Field of Classification Search
  CPC . C08H 8/00; C10G 1/00; C10G 31/06; C12M 45/02; C12M 45/06; C12M 45/20; D21C 1/02; Y02W 10/30
  See application file for complete search history.

(56) References Cited

FOREIGN PATENT DOCUMENTS

| | | |
|---|---|---|
| NO | 330122 B1 | 2/2011 |
| WO | WO-96/09882 A1 | 4/1996 |
| WO | WO-03043939 A2 | 5/2003 |

OTHER PUBLICATIONS

Grundfelt, Ingrid, "International Search Report" prepared for PCT/NO2014/000017, dated Apr. 29, 2014, 4 pages.

\* cited by examiner

METHOD AND DEVICE FOR PRETREATMENT OF BIOMASS FOR CONVERSION TO ENERGY

The present invention relates to a method for thermal pretreatment of organic material, in particular, biomass for biological energy conversion. Furthermore, the invention comprises a device for thermal pretreatment of biomass, said device encompasses a system for transport of biomass from a preheating tank to a high pressure reactor without the use of a pump and further to a pressure reduction tank and then to energy conversion.

In the internal process, thermal energy is used for transport of biomass only. The new system opens for a considerably shorter cycle time and essentially better utilisation of the reactor volume with regard to prior art. The method and device eliminate the use of pumps and level instrumentation and thereby considerably reduce cost and maintenance. The device includes a new system for the supply of fresh biomass to the preheating tank that improves the energy recovery. A main aim of the present invention is to reduce the amount of piping and valves that are subjected to wear and also eliminate the need for pumps for the transfer of biomass between the process tanks or to export to downstream energy conversion.

Thermal hydrolysis and steam explosion is a known method to break down biomass so that it is better suited to biological processes for energy conversion, such as, for example, digestion to biomass. The treatment of biomass with high temperatures occurs most often by the supply of steam at high pressure, typically 4-20 bar(g). This can be energy demanding, particularly if the biomass has a low dry matter content such as effluent sludge. To reduce the demand for energy it is important to recover as much heat as possible in the process. It can also be effective to treat the biomass at a higher dry matter content by dewatering it first. Biomass with a high dry matter content is difficult to transport in processing equipment. Large dimensions and robust solutions are required. The present invention uses thermal pressure energy only for the transport of the biomass and thereby reduces the risk for blockages or wear in the system.

There are several patented methods that describe both batch-wise and continuous processes for thermal hydrolysis. Batch-wise treatment of biomass gives acceptable sterilisation and disinfection to be able to document the required residence time at high temperature. This is different from continuous processes that can not document that all the biomass has been held long enough at the right temperature. Heating of the biomass ought to take place with the addition of fresh steam. The hydrolysis temperature, the temperature at which the biomass is treated, can normally be related to the saturation pressure of the steam in the reactor. After the thermal treatment, a fast and complete pressure reduction of the biomass is important for the use-value of the process. With a fast pressure reduction a steam explosion will take place in the biomass when the water becomes steam. Thus, the biomass is ripped apart and the required characteristics of the biomass are achieved, such as smaller particle size, a ripping apart of cell membrane and a lower viscosity.

In particular, there are two methods for batch-wise thermal hydrolysis that are known.

WO96/09882 (Solheim) describes an energy efficient process where the biomass is preheated in a preheating tank with the help of recycled steam from a downstream process in a preheating tank before the mass is pumped into one of several, parallel reactors. The biomass is supplied fresh steam for the heating and is held at a specified temperature and pressure in the reactor for the required time. Thereafter, the reactor is pressure relieved and steam is led back to the preheating tank for energy recovery. When the pressure in the reactor has sunk to a required level (typically 2-4 bar(a)), the steam return from the reactor to the preheating tank is closed. Thereafter the biomass is blown over into a pressure reduction tank at a low pressure (typically 1.2 bar(a)). The advantage with this system is that one can recover, at a relatively low pressure in the pressure reduction tank, a large part of the energy in the reactor after the thermal hydrolysis is completed. The pressure reduction in the reactor before it is blown over to the pressure reduction tank is described as necessary to reduce the erosion problems in the pipe system between the reactor and the pressure reduction tank.

U.S. Pat. No. 6,966,989 (Højsgaard) does not use a preheating tank in contrast to Solheim, but has reactors in parallel that also operate as preheating tanks. This is achieved in that a reactor at a high pressure is relieved by letting steam over into a waiting reactor at a low pressure. When the pressure in these reactors has equalised, the steam transfer is shut and the hydrolysed biomass in the reactor is blown over into a low pressure reduction tank. There is no description of energy recovery from the pressure reduction tank. By filling a reactor with steam from a second reactor, one does not come far down in pressure and the energy recovery is thereby not optimal.

Common to the two systems is the use of pumps. This limits the capacity and leads to a poor utilisation of the reactor volume. The present invention utilises the reactor volume better in that the filling takes place with the help of vacuum and gravity in short pipes of a large dimension. This gives a typically ten times faster filling than with the use of a pump. The part of the total time which the reactor is active will thereby be larger in the present system than for other known methods for batch-wise hydrolysis.

With such a fast filling it is difficult to control the process to obtain the required level in the reactor. Traditional level measuring instruments are subjected to considerable process noise in such situations. Large control valves are also too slow to be able to control such fast filling processes. In the present invention a method is included to ensure the correct level, which includes simple geometrical limitations and an analysis of a high-frequency pressure signal.

The energy efficiency of Solheim is somewhat higher than for the system of Højsgaard as the pressure in the pressure reduction tank is somewhat lower. But the pressure in the pressure reduction tank of Solheim is never lower than the required liquid height in the preheating tank which ensures condensation and energy recovery of return steam, typically 1.2-1.3 bar. The present invention improves this situation with the help of a dedicated steam return line from the pressure reduction tank of the steam phase in the preheating tank and an inlet arrangement for cold, fresh biomass which ensures optimal condensation of the return steam. The pressure in the pressure reduction tank can, in this way, become as low as typically 0.3-0.5 bar, something which leads to increased energy recovery and lower total consumption of steam.

A method and a device for treatment of biomass by the use of thermal hydrolysis are known from WO 03/043939. The biomass is preheated in a preheating step, whereupon the heating takes place with the use of fresh steam and with flash steam from a pressure reduction tank.

The above mentioned aim and advantages are obtained with respect to the present invention by a method for pre-treatment of organic material, particularly biomass, to energy conversion, said method comprises a first preheating step with a preheating tank, a hydrolysis step with a hydrolysis reactor and a pressure reduction step with a pressure reduction tank, supply organic material with a dry matter content of 5-40%, preferably 10-25% to a preheating tank, heat the organic material in the preheating tank with flash steam from a pressure reduction tank, said method is characterised in that it encompasses the following additional steps:

provide a vacuum in the hydrolysis reactor by the supply of cold water in the hydrolysis reactor, open a supply valve between the preheating tank and the reactor, transfer heated organic material from the preheating tank to the reactor with the help of a vacuum and gravity and fill this essentially full, measure the pressure in the reactor with the help of a sensitive high frequency pressure sensor that measures the pressure and analyses pressure oscillation in the reactor to detect the level, recycle surplus organic material from the reactor to the preheating tank by the supply of steam to the top of the reactor until the pressure sensor registers that the required level in the reactor has been reached, shut the supply valve between the reactor and the preheating tank, supply fresh organic material to the preheating tank, heat the organic material in the reactor by the supply of steam and maintain the desired temperature for a sufficient length of time, open a blow valve between the reactor and the pressure reduction tank and transfer the treated organic material from the reactor to the pressure reduction tank and achieve a steam explosion as a consequence of the pressure difference between the reactor and the pressure reduction tank, transfer flash steam that is released in the steam explosion in the previous step via a steam return line to below the liquid level in the preheating tank and recover the heat by steam condensation in the organic material in the preheating tank, close the steam return line and open a steam return line from the pressure reduction tank to above the liquid level in the preheating tank to reduce further the pressure difference between the pressure reduction tank and the preheating tank beyond the pressure that the liquid column in the preheating tank represents.

The invention also comprises a device for thermal hydrolysis and steam explosion of organic material, encompassing a preheating tank connected with a reactor and a pressure reduction tank connected with the reactor, which is characterised in that the preheating tank is placed vertically above the reactor, either on the same vertical axis as the reactor or in parallel with this.

Further advantageous features of the method and the device are given in the dependent claims.

The invention will be described in more detail in the following with the help of an embodiment example with reference to the enclosed figures, where FIG. 1 shows schematically an embodiment of a device for pretreatment of organic material to energy conversion according to the invention;

Figure 1:
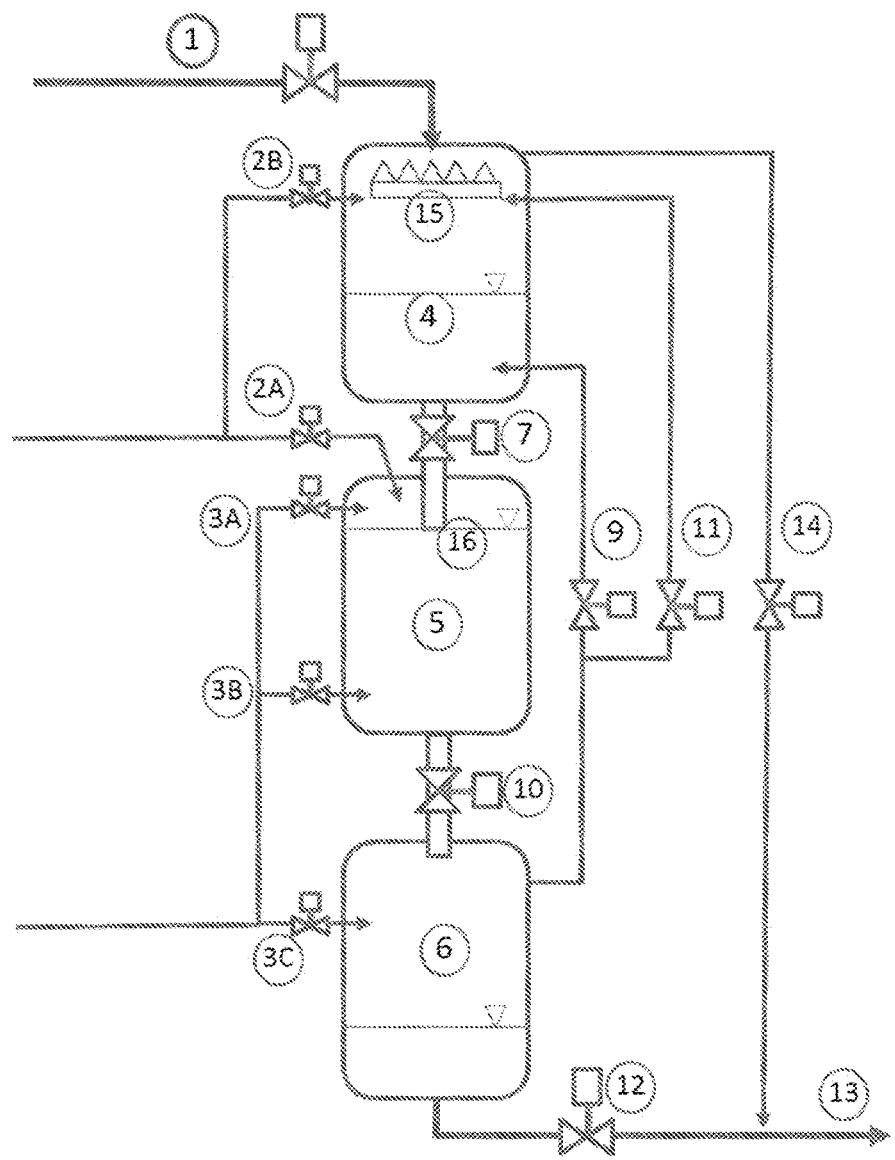
FIG. 1 shows schematically an embodiment of a device for pretreatment of organic material according to the present invention.

Three tanks are connected in series; a preheating tank 4, a reactor 5 and a pressure reduction tank 6. The volume of the preheating tank 4 and the pressure reduction tank 6 is typically twice as large as the volume of the reactor 5. The preheating tank 4 and the reactor 5 can be placed directly above each other to reduce the piping to a minimum and use gravity for the transfer of the biomass from the one tank to the other. Alternatively, the preheating tank 4 can be placed essentially in parallel with the vertical axis of the reactor 5. The tanks can be isolated with valves. It is possible to supply steam to the reactor 5 and the pressure reduction tank 6. There are two steam return lines from the pressure reduction tank 6 to the preheating tank 4 to recover thermal energy supplied in the reactor 5 by thermal hydrolysis. There is a gas export pipe from the preheating tank to the export line 13 for organic material. An inlet arrangement 15 that breaks up the organic material is in the preheating tank 4, and supplies this with a large surface area.

Organic material 1, for example, biomass with a typical dry matter content of 5-40%, preferably 10-25%, is pumped into a preheating tank 4, possibly via a device 15 that increases the contact surface between the biomass and the steam in the pretreatment tank 4, and is preheated by flash steam from a pressure reduction tank 6, typically 80-100° C. After sufficient heating the biomass is thereafter led to a reactor 5. This is carried out by generating a vacuum in the reactor before the filling valve 7 between the preheating tank 4 and the reactor 5 opens. The vacuum is generated by condensing the steam that remains in the reactor 5 after the previous emptying of biomass from the reactor 5 to the pressure reduction tank 6. Condensation of steam takes place by injecting cold water 2A at the top of the reactor 5. (Typically, 50 liters will be able to condense all the steam and generate a full vacuum.) The preheating tank 4 can be placed directly above the reactor 5, either in the vertical axis of the reactor 5 or in parallel with it. When the filling valve 7 opens the vacuum in the reactor 5 and the pressure from the liquid column in the preheating tank 4 will result in a very fast transfer of the biomass from the preheating tank 4 to the reactor 5. A typical fill time is 10-180 seconds, preferably 20-40 seconds. This is much faster than other known solutions. Traditionally control valves and level measuring instruments are used for the control of the reactor volume. This is not possible for such fast filling, as with this apparatus. The correct level is ensured in the present invention in a different way.

The reactor 5 is completely filled. This is in principle not to be desired as there must be some space for fresh steam that condenses during the subsequent heating of the biomass in the reactor 5, typically 10-30% of the reactor volume. This is solved in the present invention in that the fill pipe 16 from the preheating tank 4 to the reactor 5 ends at a defined height inside the reactor. This height defines the desired fill volume in the reactor 5 before the heating of the biomass commences. The necessary expansion volume above the biomass is then ensured by supplying fresh steam 3A at the top of the reactor 5 while the filling valve 7, between the preheating tank 4 and the reactor 5, is still open. Thus the surplus biomass flows back into the preheating tank 4 before the filling valve 7 between the tanks is closed.

This volume can alternatively be provided by a side-mounted valve and an external line to the preheating tank 4.

The present invention minimises the use of steam for level control of the reactor 5. Surplus biomass is out of the reactor 5 and the filling valve 7 closes when a sensitive, high frequency pressure sensor (not shown in the figures) in the reactor 5 indicates that steam is let out of the reactor and up into the fill pipe 16 to the preheating tank 4. This is detected by pressure oscillations when the steam bubbles from the reactor 5 condense and collapse in the fill pipe. A high frequency registering of the pressure in the reactor connected with an analysis of the pressure oscillations are used to determine that the required level has been reached in the reactor 5. In this way one eliminates the need for complex level measuring instrumentation in the reactor 5.

Figure 2:
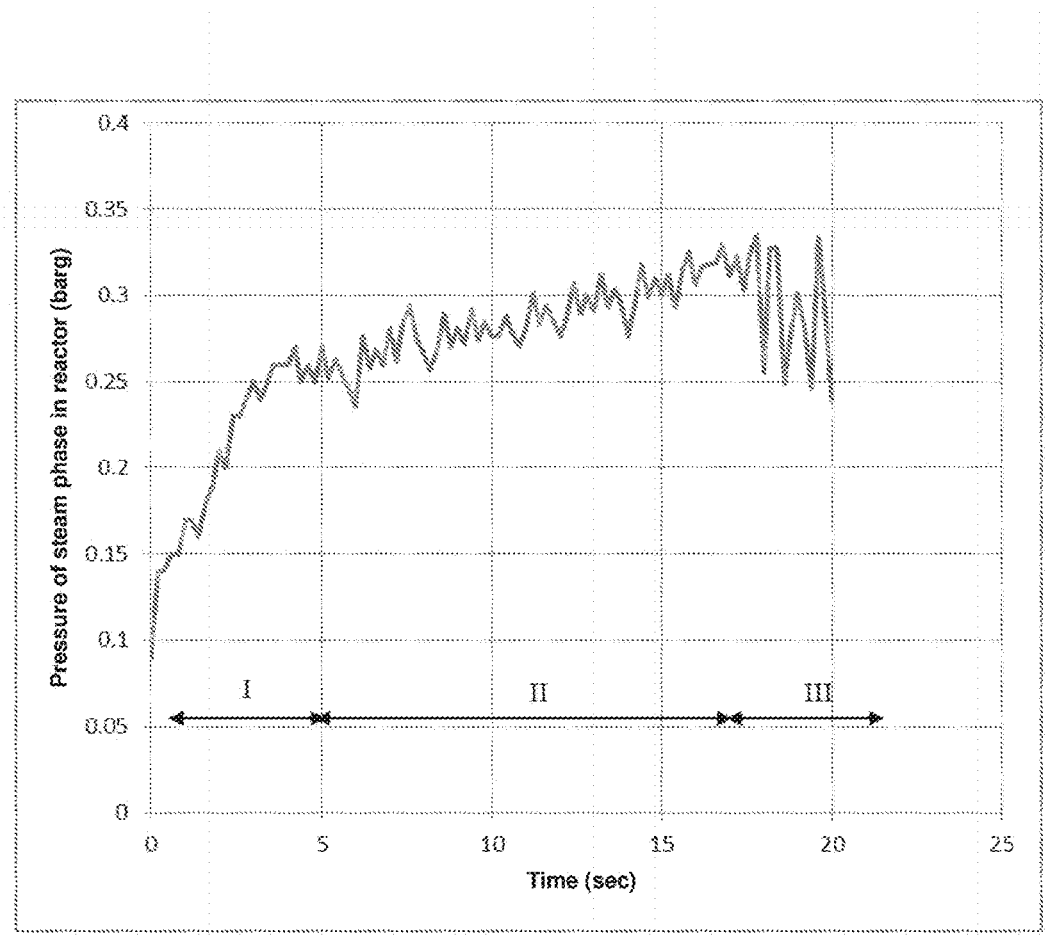
FIG. 2 shows an example of a pressure signal by the return of surplus organic material from the reactor to the preheating tank.

FIG. 2 shows a typical pressure signal at the return of surplus biomass from the reactor 5 to the preheating tank 4. The pressure increases quickly in the start phase (shown by I in FIG. 2) when the steam accelerates the biomass from the reactor 5 up into the fill pipe 16. The sludge starts to flow back to the preheating tank 4. The pressure increases more evenly (shown by II in FIG. 2), while the biomass is returned to the preheating tank 4 and the static pressure between the reactor and the preheating tank increases in that the liquid level in the preheating tank 4 increases and the liquid level in the reactor 5 decreases.

When the liquid level in reactor 5 is sunk to the end of the fill pipe 16, steam from the top of the reactor will go up the fill pipe to the preheating tank. This steam rises up into colder biomass and will condense. This creates larger pressure pulses (shown by III in FIG. 2). These pulses indicate that the reactor 5 has the right liquid level before the heating of the biomass can start.

The biomass in the reactor 5 is heated up to the desired hydrolysis pressure, typically 3-16 bar, preferably 3-7 bar for the treatment of effluent sludge and wet organic waste, preferably 10-12 bar for the treatment of prion-containing biomass and preferably 12-16 bar for the treatment of lignocellulose-containing biomass, by the supply of fresh steam 3B to the reactor 5, and is thereafter held at this pressure for a predetermined time, typically 20-30 minutes for the treatment of effluent sludge and wet organic waste, preferably 60-120 minutes for the treatment of prion-containing biomass and preferably 5-20 minutes for the treatment of lignocellulose-containing biomass. Thereafter, the blowing valve 10 is opened and the biomass is blown from the reactor 5 at high pressure to the pressure reduction tank 6 at low pressure. Thereby a steam explosion takes place in the biomass. The flash steam that is released in the steam explosion in the pressure reduction tank 6 is led back to below the liquid level in the preheating tank 4 via a pressure reduction pipe 9. The surplus heat from the pressure reduction tank 6 is recovered by the steam condensation in the biomass in the preheating tank 4.

After the reactor 5 has been emptied, the blow valve 10 is closed and it is ready for a new filling of the reactor 5.

An advantage with a one-reactor system is that one can use the preheating tank 4 and the pressure reduction tank 6 for other purposes while the reactor 5 is filled with biomass for thermal hydrolysis. As soon as the blow valve 10 is closed and the pressure between the pressure reduction tank 6 and preheating tank 4 is in balance via the steam return line 9, this is closed and a steam return line 11 is opened from the pressure reduction tank 6 to the gas phase in the preheating tank 4. Thereby, the pressure difference between the pressure reduction tank 6 and the preheating tank 4 can be reduced beyond the pressure which the liquid column in the preheating tank 4 represents, this gives a typical 0.1-0.2 bar further reduction. This means that the pressure in the pressure reduction tank 6 is independent of the liquid level in the preheating tank 4. The lower the pressure in the pressure reduction tank 6, the lower the temperature of the biomass that goes out of the pressure reduction tank 6. At the same time as the steam return line 11 is open, new biomass 1 is pumped into the top of the preheating tank 4. This biomass is cold, typically 5-40° C. The steam in the preheating tank 4 is condensed on the new biomass, the biomass is preheated and reduces the pressure in the preheating tank 4 and the pressure reduction tank 6 further. This is an important function for optimal energy efficiency.

To optimise the steam condensation on the new biomass a device 15 is placed in the preheating tank 4 that gives the biomass a large contact surface with the gas phase in the preheating tank 4. The device 15 breaks up the biomass into thin film fragments or beams.

The level in the pressure reduction tank 6 must be reduced sufficiently before the next emptying of the reactor 5. This takes place by closing the steam return line 11 and filling fresh steam 3C into the gas phase of the pressure reduction tank 6. When the pressure is sufficient (typically 2-4 bar) to transport the treated biomass to desired downstream equipment via the outlet pipe 13, the outlet valve 12 is opened and the level in the pressure reduction tank 6 is reduced to the required minimum level before the outlet valve 12 closes again.

Volatile and inert process gasses are released, which are formed during the thermal pretreatment that takes place in the reactor 5. These gases are transported via the pressure reduction tank 6 to the preheating tank 4. The process gases must be removed from the hydrolysis plant to prevent accumulation and reduced efficiency of the plant. Normally these gases will be sent to biological degradation via the outlet pipe 13.

Before new biomass is supplied to the preheating tank 4, the process gas from the preheating tank 4 will be led to the outlet pipe 13 via the process gas pipe 14. This process gas pipe 14 is opened when the pressure in the preheating tank 4 is sufficiently high, typically 2-4 bar. The required pressure is reached with the supply of fresh steam 3C to the pressure reduction tank 6. When the process gas has been vented out via the process gas pipe 14, this closes. The steam return line 11 closes.

Before the next emptying of the reactor 5 to the pressure reduction tank 6, it is important that the pressure in the preheating tank 4 is as low as possible to recover as much flash steam as possible. This is achieved by steam condensation in the preheating tank 4 by injecting cold water 2B into this. The low pressure in the preheating tank 4, and thereby in the pressure reduction tank 6, results in an increased amount of flash steam from the biomass in the pressure reduction tank 6 and thereby the lowest possible temperature of the biomass in the outlet 13.

Figure 3:
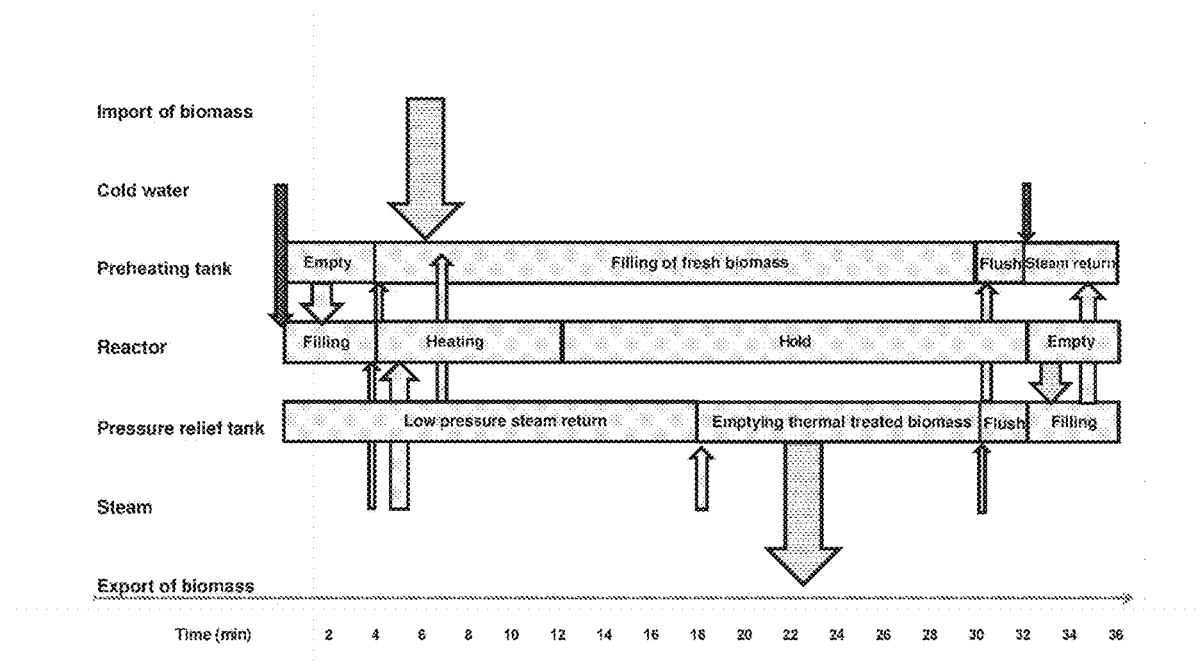
FIG. 3 shows schematically an example of the sequence.

FIG. 3 shows schematically an example of a typical sequence for the three tanks.

The invention claimed is:
1. An organic-material pretreatment method comprising:
supplying organic material with a dry matter content of 5-40% to a preheating tank;
heating the organic material in the preheating tank with flash steam from a pressure reduction tank;
providing a vacuum in a hydrolysis reactor by supply of cold water to the hydrolysis reactor;
opening a supply valve between the preheating tank and the hydrolysis reactor;
supplying steam to the top of the hydrolysis reactor so that surplus organic material flows back from the hydrolysis reactor to the preheating tank via a pipe fitted with the supply valve, the pipe connecting the preheating tank with the hydrolysis reactor, the pipe sticking some distance into the hydrolysis reactor, a lower end of the pipe defining a required filling level in the hydrolysis reactor;

transferring the heated organic material from the preheating tank to the hydrolysis reactor with help of vacuum and gravity;

measuring pressure in the hydrolysis reactor and analysing pressure oscillations in the hydrolysis reactor to detect a level of the organic material in the hydrolysis reactor;

recycling surplus organic material from the hydrolysis reactor to the preheating tank with a supply of steam to a top of the hydrolysis reactor until the pressure registers that a required level in the hydrolysis reactor has been reached;

closing the supply valve between the hydrolysis reactor and the preheating tank;

supplying new organic material to the preheating tank;

heating the new organic material in the hydrolysis reactor by a supply of steam;

maintaining a desired temperature for a sufficient length of time;

opening a blow valve between the hydrolysis reactor and the pressure reduction tank and transferring the new organic material from the hydrolysis reactor to the pressure reduction tank and obtaining a steam explosion as a consequence of a pressure difference between the hydrolysis reactor and the pressure reduction tank;

leading the flash steam released in the steam explosion via a steam return line to under a liquid level in the preheating tank;

recovering heat by steam condensation in the new organic material in the preheating tank; and closing the steam return line; and opening a steam return line from the pressure reduction tank to above the liquid level in the preheating tank to further reduce the pressure difference between the pressure reduction tank and the preheating tank beyond a pressure the liquid level in the preheating tank represents.

2. The organic-material pretreatment method according to claim 1, comprising increasing the contact surface between the organic material supplied to the preheating tank and the steam in the preheating tank.

3. The organic-material pretreatment method according to claim 1, wherein the organic material in the preheating tank is heated to 80-100° C.

4. The organic-material pretreatment method according to claim 1, wherein the required level in the hydrolysis reactor is detected by high frequency registering of the pressure in the hydrolysis reactor combined with pressure oscillation analysis.

5. The organic-material pretreatment method of claim 1, wherein the organic material has a dry matter content of 10-25%.

* * * * *